United States Patent [19]
Milner

[11] Patent Number: 5,888,441
[45] Date of Patent: Mar. 30, 1999

[54] PREPARATION OF ANTIMICROBIAL ARTICLES

[75] Inventor: Richard Milner, Bishops Stortford, United Kingdom

[73] Assignee: Ansell Healthcare Products Inc., Massillon, Ohio

[21] Appl. No.: 49,613

[22] Filed: Apr. 16, 1993

Related U.S. Application Data

[63] Continuation of Ser. No. 659,395, Feb. 21, 1991, abandoned.

[30] Foreign Application Priority Data

Aug. 24, 1988 [WO] WIPO ................................ 8820108
Sep. 7, 1988 [WO] WIPO ................................ 8820945
May 17, 1989 [WO] WIPO ................................ 8911326

[51] Int. Cl.$^6$ ............................. A61L 31/00; A61B 19/04
[52] U.S. Cl. ........................... 264/255; 264/306; 264/307; 264/308
[58] Field of Search ..................... 264/255, 306, 264/307, 308, DIG. 30; 427/2; 424/404; 2/167, 168; 604/292, 304

[56] References Cited

U.S. PATENT DOCUMENTS

| | | | |
|---|---|---|---|
| 3,987,797 | 10/1976 | Stephenson | 424/404 |
| 4,143,109 | 3/1979 | Stockum | 264/308 |
| 4,499,154 | 2/1985 | James et al. | 2/168 |
| 4,675,347 | 6/1987 | Mochizuki et al. | 523/122 |
| 4,678,660 | 7/1987 | McGary et al. | 604/304 |
| 4,713,402 | 12/1987 | Solomon | 523/112 |
| 4,853,978 | 8/1989 | Stockum | 604/292 |
| 5,031,245 | 7/1991 | Milner | 2/168 |
| 5,089,205 | 2/1992 | Huang et al. | 264/308 |

*Primary Examiner*—Mathieu D. Vargot
*Attorney, Agent, or Firm*—Gardner, Carton & Douglas

[57] ABSTRACT

A method for the manufacture of an antimicrobial rubber article which includes incorporating an effective amount of an antimicrobial agent into the natural rubber after the article has been shaped but before the article has been cured is disclosed.

10 Claims, No Drawings

PREPARATION OF ANTIMICROBIAL ARTICLES

This application is a continuation of application Ser. No. 07/659,395, filed Feb. 21, 1991, now abandoned.

This invention relates to antimicrobial articles and more particularly to gloves such as the type of gloves worn by medical practitioners such as surgeons, nurses and other medical or paramedical personnel, to their manufacture and to their use.

Conventionally surgical gloves are manufactured from extremely thin elastomeric materials such as natural or synthetic rubbers. These gloves fit closely and tightly over the users hand. One disadvantage which is experienced with this type of glove is that they are sometimes punctured or ruptured in use. The presence of any small hole such as that caused by a surgical needle or other surgical instrument can result in contamination and infection at the operation site by transfer of bacteria from the inside of the glove to the open wound or the surgical instruments. Also if body fluids of the patient carry viable bacteria or viruses these may penetrate through a discontinuity in the glove and if they contact broken skin can cause infection of the surgical personnel involved. It has been suggested that channels can exist in latex gloves which allow viruses to pass through. Although it is the custom for the medical personnel to scrub their hands vigorously with an anti-infective skin cleanser before donning gloves, the anti-infective effect may be short lived and infective agents such as bacteria may regrow beneath the gloves in the moist warm environment. If a glove is punctured in use it may not be recognised and the operation is continued allowing risk of infection.

It has been suggested that a way of protecting the user of a glove is to provide a coating containing an anti-infective agent (see European Patent Publication No. 300814). A secure method of protection is required which does not rely upon maintaining the integrity of a coating both during manufacture and use. Such as method has now been discovered.

It has now been found that by immersing a coagulated but uncured glove shape formed from a natural rubber latex in a solution of an antimicrobial agent such as an aqueous solution of a water soluble ionic antimicrobial agent for example chlorhexidine digluconate, the antimicrobial agent is incorporated in the latex without adverse effect thereto. The antimicrobial agent is dispersed throughout the glove material and is observed to release an antimicrobially effective amount of the antimicrobial agent from either surface of the glove. The risk of infection to the patient and glove wearer is reduced.

It is surprising that surface treatment of what will become the inner surface of the glove at this stage of its transformation into a glove yields a glove in which the antimicrobial agent is dispersed throughout the glove material. The antimicrobial agent is not restricted to a coating on the surface which becomes the inside of the glove. Microscopic examination of the inner and outer surface of the glove does not show evidence of a coating on either.

The level of antimicrobial agent available on the skin of the wearer is sufficient to inhibit many common bacteria and also to help to inhibit certain viruses. It is also believed that such a level would be sufficient to provide an improved barrier to infective agents including certain viruses such as the human immunosuppressive virus (H.I.V.).

An alternative way of coping with microbes was suggested in U.S. Pat. No. 4,675,347 in which it was disclosed that although chlorhexidine salts caused gellation of natural rubber latices it was possible to use chlorhexidine salts in cationic latex. Unfortunately it is not always convenient or practicable to employ cationic latex in the manufacture of rubber articles and so it is desirable to have a process available which can use ordinary natural rubber latex.

The present invention is based on the discovery that the drawbacks of the above cited methods (that is the problem with having a layer as in said European Patent Specification or having to use cationic latex as in said U.S. Patent Specification) can be avoided if an article made from natural rubber latex (ie non cationic) is treated with a antimicrobial agent such as chlorhexidine salt such as chlorhexidine digluconate in the "green state" or the "wet gel state", that is the state after the article has been formed but before it is cured.

The present invention provides a method for the manufacture of an antimicrobial rubber article which method comprises incorporating an effective amount of antimicrobial agent into the natural rubber latex after the article has been shaped but before the article has been cured.

This invention is most advantageous for the manufacture of gloves such as surgeon's gloves or examination gloves, but is also applicable to other rubber articles such as condoms, catheters such as urethral catheters, wound drains, endotracheal tubes, feeding tubes and the like. The benefits of the invention are most marked for thin walled articles such as gloves and condoms where improved barrier properties are particularly desired especially in view of the increasing occurance of virus diseases such as those resulting from infection by human immunosupressive virus.

A shaped but not yet cured rubber article is one which has taken up the desired configuration (for example by dipping a former of the desired configuration into the latex) and which is no longer water dispersible. A cured article is one which has dried and is normally fully vulcanised.

Rubber articles can be formed by dipping process which employ a coagulant and by processes which do not employ a coagulant. However, the method of this invention is particularly suitable for the manufacture of rubber articles by a process which employs a coagulant because problems with washing off insufficiently gelled latex from the former when the antimicrobial agent is being introduced are effectively avoided.

Thus in a favoured aspect the present invention provides a method for the manufacture of an antimicrobial rubber article which method comprises incorporating an effective amount of an antimicrobial agent into the natural rubber latex after the article has been formed by dipping a coagulant coated former into natural rubber latex but before the article has been cured.

This version of the method of the invention is most suitably empoyed in the manufacture of gloves such as surgeon's gloves and examination gloves.

In the process of this invention it is desirable to incorporate a leaching step between the forming of the article and the incorporation of the antimicrobial agent. Thus in a preferred aspect this invention provides a method of manufacture of an antimicrobial rubber glove which includes the step of incorporating an antimicrobial agent into the natural rubber latex between the leaching and curing step in the glove forming process.

The incorporation of the antimicrobial agent is best achieved by dipping the green stage latex coated former into a solution of the antimicrobial in water. This is most aptly done at ambient temperatures for example at 20° C.

The manufacture of the gloves may be initiated as is conventional in the art by forming a coating of a coagulant on a heated glove shaped former. The coated former is then dipped into a natural rubber latex, withdrawn and then dipped into a warm water leach bath. After removal from the leach bath, the glove shape is dipped into a solution of an antimicrobial agent. After dipping the glove-shape is cured. Then it may be coated with a lubricating donning powder and stripped from the former. By being able to apply an antimicrobial agent in this way more complex processes of forming medicated rubber articles such as gloves are avoided. These complex processes include those processes which require swelling and deswelling the finished article with solvents in the presence of an active agent or which require the preparation of special medicated dusting powders or which provide coatings of the antimicrobial agent with special bonding agents.

The present invention also provides an antimicrobial glove which has incorporated in it an antimicrobial agent using the process hereinbefore described.

The antimicrobial agent can be a water soluble antimicrobial agent and is preferably an ionic antimicrobial agent. Suitably the antimicrobial agent can have a solubility in water of greater than 0.1 g/100 g of water and more suitably greater than 1.0 g/100 g and preferably greater than 10 g/100 g of water (the solubilities may be measured at ambient temperatures, for example 20° C.). Suitable antimicrobial agents include quaternary ammonium antimicrobial agents and chlorhexidine salts especially chlorhexidine digluconate and chlorhexidine diacetate of which chlorhexidine digluconate is preferred.

Accordingly the present invention provides a glove which has at least a portion of the inner surface thereof surface (ie. the wearer facing side) treated with chlorhexidine digluconate.

It is clear from the above that surface treatment during the glove forming process of the surface which becomes the inner surface of the glove with chlorhexidine digluconate solution results, after curing, in an antimicrobial natural rubber latex glove. The glove has incorporated throughout it chlorhexidine digluconate. The glove is stable on storage. This is surprisingly advantageous since instability in natural rubber latex is observed if, for example a multivalent ionic material such as chlorhexidine digluconate is mixed with it. It is particularly surprising that the chlorhexidine digluconate does not simply remain on the treated surface but finds its way into the bulk of the rubber.

Accordingly in another aspect the present invention provides an antimicrobial rubber glove in which is incorporated throughout an antimicrobially effective amount of chlorhexidine digluconate.

It is very surprising that chlorhexidine digluconate is suitable for incorporating in a glove since it is a hygroscopic or even deliquescent solid and is usually only available as a solution. The treated gloves retain their antimicrobial properties and are stable on storage. The chlorhexidine digluconate appears not to effect any lubricating powder present by, for example, absorbing moisture onto the inner suface of the glove.

In a preferred aspect of the invention an antimicrobial glove formed by the process may contain a second antimicrobial agent. Aptly this second agent will be incorporated in the glove material when in the form of the natural rubber latex. Suitable antimicrobial agents include non-ionic, sparingly water soluble antimicrobial agents for example halogenated hydroxy diphenyl derivatives such as 2,4,4'-trichloro-2'-hydroxy diphenyl ether (triclosan).

Aptly the halogenated hydroxy diphenyl derivative is a diphenyl ether. A particularly suitable diphenyl ether is 2,4,4$^1$-trichloro-2$^1$-hydroxy diphenyl ether (triclosan).

In another aspect the present invention provides an antimicrobial glove which contains a halogenated hydroxy phenyl derivative and a chlorhexidine salt.

In a further aspect the invention provides a glove which contains a halogenated hydroxy diphenyl derivative and is surface treated on at least a portion of its inner surface with chlorhexidine digluconate.

Such derivatives may be mixed with the glove material prior to forming the glove-shape. Suitably the glove material will contain an antimicrobially effective amount of the derivative. Suitably the glove material may contain from 0.1 to 10% w/w of the derivative, more suitably 0.5 to 5% w/w and preferably 1 to 4% w/w, for example, 1%, 2%, 3% and 4%.

The gloves may be used as surgeon's gloves, as examination gloves or for any other purpose which it is desired to reduce the risk of infection. Aptly the glove is a surgeon's glove. Aptly the glove is an examination glove.

The antimicrobial agent such as chlorhexidine digluconate may be applied to the glove by dipping the glove-shape when on its former into an appropriate strength solution of the antimicrobial agent. Suitably the solution may contain from 0.05 to 25% by weight and more suitably from 0.1 to 10% by weight, for example 0.1%, 2%, 4%. These figures are particularly suitable for chlorhexidine digluconate. The amount of time the glove material spends in the solution depends upon the strength of the solution and the amount of the antimicrobial agent required in the glove. Typically a 1 or 2 minute dip in a 4% w/w aqueous solution chlorhexidine digluconate incorporates sufficient of the antimicrobial agent into the glove material, that is 3% w/w from a 1 minute dip and 4% w/w from a 2 minute dip.

The amount of antimicrobial agent incoporated in the glove by dipping process can be from 0.1 to 10% by weight, more suitably can be 0.5 to 8% and is preferably 1 to 6%, for example 2 to 4%.

The use of a natural rubber latex to form the glove material is preferred. The use of this process to incorporate chlorhexidine salts in a natural rubber latex glove offers a method of overcoming many of the potential problems which could occur with natural rubber latex gloves if they are susceptable to penetration by viruses such as those responsible for AIDS and Hepatitis B.

It will be understood that in a preferred aspect this invention provides a thin rubber glove which contains chlorhexidine salt such as chlorhexidine digluconate. Such gloves offer the user a high degree of protection from common infecting organisms that might penetrate through any discontinuity in the glove. The use of such gloves can reduce the need for extensive pre-sterilisation of the skin as the antibacterial agent is effective in reducing skin flora especially after wet glove donning.

The present invention provides a method of reducing the risk of infection which comprises using thin polymer gloves which have incorporated therein by surface treatment thereof an antimicrobially effective amount of chlorhexidine digluconate. Most aptly the gloves are donned onto wet (or at least damp) hands.

The use of a glove which has incorporated in it chlorhexidine digluconate and which also contains triclosan provides antimicrobial protection for the wearer for an extended period, for example up to 6 to 8 hours.

In a further aspect this invention provides a method of reducing the risk of infection which comprises using at least two pairs of thin rubber gloves which each contain an antimicrobial agent such as a chlorhexidine salt such as chlorhexidine digluconate.

In these further aspects of the invention the glove material may contain a second antibacterial agent as hereinbefore described.

The gloves of the present invention may be prepared by taking a glove former, heating it and dipping into a conventional coagulant solution. The former is removed and air-dried. The coated former is then immersed in a solution of the glove material. Preferably this is a pre-vulcanised natural rubber latex for example, 42% solids, aqueous dispersion and optionally containing a second antibacterial agent. The coated former is then withdrwawn, air-dried for about 2 minutes and immersed in a leach tank of warm water, at about 70° C., for about 2 minutes to extract any water soluble material. The former is removed and then immersed in an aqueous solution containing an appropriate concentration of the antimicrobial agent such as chlorhexidine digluconate. The glove-shape may be immersed for a period of between 10 seconds and 5 minutes, and more suitably 30 seconds to 4 minutes, depending on the strength of the solution. The glove is 'cured' in an oven, and may be dusted with lubricating powder before it is stripped from the former, everting the glove so that the antimicrobial surface treated surface forms the inner surface of the glove.

In a further preferred aspect therefore the present invention provides a method of making a glove which method comprises forming a coating of the glove material on a glove-shaped former, immersing the former in a solution of chlorhexidine digluconate, withdrawing it from the solution, optionally curing the glove material, optionally dusting the glove-shape with lubricating powder, stripping the glove from the former, thereby everting the glove so that the chlorhexidine digluconate treated surface forms the inner surface of the glove.

Preferably the glove material comprises a natural rubber. The coating on the former is obtained by dipping the former in a latex of pre-vulcanised natural rubber.

In a further aspect the invention represents an improvement in the method of manufacture of an antimicrobial rubber latex glove by (a) forming a dry coating of coagulant on a glove shaped former, (b) immersing the coated former in natural rubber latex, (c) leaching the coagulated latex in water, (d) curing the leached, coagulated latex to form the glove, the improvement comprising dipping the leached coagulated latex into a solution of an antimicrobial agent between the leaching and curing steps in the glove forming process. In this process the leaching step may be carried out at the same time as incorporating the antimicrobial agent (ie. the solution of the antimicrobial agent may be the leach bath) if desired.

Analogous methods to those hereinbefore described can be employed to prepare other shaped rubber articles.

EXAMPLE 1
Preparation of a Glove

A glove-shape was prepared in a conventional manner by coagulating a rubber latex on to a glove-shaped former and then leaching in a tank of warm water at 70° C. for two minutes. After leaching the former was dipped in an aqueous solution containing 10% w/w of chlorhexidine digluconate for 20 seconds and then removed and shaken to remove adhering water droplets. The glove-shape was cured by placing in an over at 115° C. for 25 minutes, cooled, dusted with cross-linked cornstarch and stripped from the former causing the glove-shape to evert.

A sample of glove material prepared by the method described in Example 1 which had been immersed in various concentrations of chlorhexidine digluconate was placed with the treated surface contacting the surface of an agar growing medium seeded with *Staphyloccocus aureus*. The plate was incubated and a zone of inhibition of growth of the bacteria around the samples was observed indicating successful release of the antibacterial agent. The results are shown in the following table:

| Percentage of Chlorhexidine Digluconate in Dip Solution | zone of Inhibition (mm) |
| --- | --- |
| 0 (control) | 0.74 |
| 1 | 3.54 |
| 5 | 5.35 |
| 10 | 6.33 |

EXAMPLE 2
Preparation of a Glove

A glove-shape was prepared in a similar manner to Example 1 except that the rubber latex contained 1% approx. by weight of triclosan. Triclosan is incorporated into the rubber latex by mixing the triclosan (21 g) with a small quantity of latex to form a paste. The paste is gradually diluted with more latex (4870 g) until the required concentration is achieved. The glove material after coagulation and leaching was dipped in a 4% queous solution of chlorhexidine digluconate for 1 minute and then cured. A sample of this antimicrobial glove material was tested in a similar manner to that described in Example 1 and gave a zone of inhibition of 5.64 mm.

EXAMPLE 3
Preparation of a Glove

A dispersion of triclosan in water (at 40% solids) was formed by ball milling for 5 hours the following mixture:

| | |
| --- | --- |
| Triclosan | 100 g |
| DARVAN No.1* | 20 g |
| Ammonium Caseinate (10% soln.) | 20 g |
| Water | to 250 g |

*sodium salts of polymerised alkylnaphthalene sulphonic acid (25% solution)

This dispersion was mixed with an aqueous rubber latex (solids content 41.5%) in the following proportions:

| | |
| --- | --- |
| 40% Triclosan dispersion | 8.3 g |
| Latex | to 800 g |

The two components were mixed until a homogenous mixture was achieved.

A glove was then prepared from the rubber latex incorporating triclosan by a similar method to that described in Example 1 so that the finished glove contains both chlorhexidine digluconate and triclosan.

I claim:

1. A method for the manufacture of an antimicrobial rubber article formed from a natural rubber latex which method comprises incorporating an effective amount of an antimicrobial agent, throughout the natural rubber latex after the article has been shaped or formed but before the article has been cured by dipping a glove shape of uncured natural rubber latex into a solution of an antimicrobial agent.

2. A method for the manufacture of an antimicrobial rubber glove formed from a natural rubber latex, including the step of incorporating an effective amount of an antimicrobial agent throughout the natural rubber latex after the article has been shaped or formed by dipping a glove shape of uncured natural rubber latex into a solution of an antimicrobial agent between a leaching and curing step, the leaching step following a forming step in a glove forming process.

3. A method as claimed in claim 2, in which the glove shape is dipped into an aqueous solution of an ionic antimicrobial agent.

4. A method as claimed in claim 3, in which the aqueous solution contains from 0.1 to 10% by weight of chlorhexidine digluconate.

5. A method as claimed in claim 1 in which the natural rubber latex has incorporated throughout it a non-ionic, sparingly water soluble antimicrobial agent.

6. A method as claimed in claim 5 in which the natural rubber latex incorporates from 0.1 to 10% of $2,4,4^1$-trichloro-$2^1$-hydroxydiphenyl ether.

7. In a method of manufacturing an antimicrobial rubber latex glove by:
  (a) forming a dry coating of coagulant on a glove shaped former,
  (b) immersing the coated former in natural rubber latex,
  (c) leaching the coagulated latex in water,
  (d) curing the leached, coagulated latex to form the glove, the improvement comprising dipping the leached coagulated latex into a solution of an antimicrobial agent between the leaching and curing steps in the glove forming process thereby to incorporate said antimicrobial throughout the latex.

8. A method as claimed in claim 7 wherein the antimicrobial agent is chlorhexidine digluconate.

9. A method as claimed in claim 7 wherein the antimicrobial is $2,4,4^1$-trichloro-$2^1$-hydroxydiphenyl ether.

10. A method of manufacturing an antimicorbial rubber latex glove comprising the steps of:
  (a) forming a dry coating of coagulant on a glove shaped former;
  (b) immersing the coated former in natural rubber latex;
  (c) leaching the coagulated latex in an aqueous solution of antimicrobial;
  (d) curing the leached, coagulated latex to form the glove; thereby incorporating the antimicrobial throughout the latex.

* * * * *